United States Patent [19]

Wallau et al.

[11] Patent Number: 5,365,002
[45] Date of Patent: Nov. 15, 1994

[54] CRYSTALLINE ZEOLITE-LIKE GALLOSILICATE, AND METHOD FOR ITS SYNTHESIS

[75] Inventors: Martin Wallau, Mainz; Rudolf Spichtinger, Frankfurt; Klaus K. Unger, Bensheim; Arno Tissler; Roland Thome, both of Bonn, all of Germany

[73] Assignees: VAW Aluminium AG, Bonn; Veba OEL AG, Gelsenkirchen-Hassel, both of Germany

[21] Appl. No.: 903,792

[22] Filed: Jun. 24, 1992

[30] Foreign Application Priority Data

Jun. 25, 1991 [DE] Germany .................. 4120847

[51] Int. Cl.$^5$ .................. C07C 2/76; C01B 33/20; B01J 29/04
[52] U.S. Cl. .................. 585/418; 585/407; 585/417; 423/326; 423/333; 502/61; 502/70
[58] Field of Search .............. 423/DIG. 22, 700, 713, 423/326, 333; 585/407, 418, 417; 502/61, 70

[56] References Cited

U.S. PATENT DOCUMENTS

| | | | |
|---|---|---|---|
| 4,585,641 | 4/1986 | Barri et al. | 502/61 |
| 4,606,900 | 8/1986 | Kacirek et al. | 423/329 |
| 4,803,060 | 2/1989 | Occelli | 423/326 |
| 4,968,650 | 11/1990 | Chu et al. | 423/DIG. 22 |
| 5,273,737 | 12/1993 | Wallau et al. | 502/61 |

FOREIGN PATENT DOCUMENTS

| | | |
|---|---|---|
| 0094288 | 11/1983 | European Pat. Off. |
| 0150256 | 8/1985 | European Pat. Off. |
| 0323893 | 7/1989 | European Pat. Off. |
| 0327189 | 8/1989 | European Pat. Off. |
| 0443539 | 8/1991 | European Pat. Off. |
| 1563559 | 4/1969 | France |

OTHER PUBLICATIONS

Derwent Abstract for EP 443,539.
Derwent Abstract for EP 44,288.

Primary Examiner—Anthony McFarlane
Attorney, Agent, or Firm—Darby & Darby

[57] ABSTRACT

The invention relates to a crystalline zeolite-like gallosilicate having an atomic ratio of Si/Ga in the outer crystalline surface that is not larger than the average Si/Ga ratio for the whole of the crystal. The invention also relates to a method of making such a gallosilicate comprising the hydrothermal crystallization of a strictly inorganic reaction mixture having the following molar ratios: $SiO_2/Ga_2O_3 \geq 5$; $OH^-/SiO_2 = 0.05-1.0$; and $H_2O/SiO_2 = 10-1,000$. The invention further relates to the above-described method wherein said reaction mixture is prepared by adding an aged gel to a first mixture, the first mixture preferably having a composition with the following molar ratios: $SiO_2/Ga_2O_3 \geq 5$; $OH^-/SiO_2 = 0.05$ to $1.0$; and $H_2O/SiO_2 = 20$ to $100$.

9 Claims, 2 Drawing Sheets

CRYSTALLINE ZEOLITE-LIKE GALLOSILICATE, AND METHOD FOR ITS SYNTHESIS

FIELD OF INVENTION

The present invention relates to crystalline zeolite-like gallosilicates, to a method for their synthesis, and to their use in the preparation of catalysts and adsorbents, particularly of catalysts for the conversion of short-chain hydrocarbons.

BACKGROUND OF THE INVENTION

Zeolite-like gallosilicates ("ZAGs") crystallographically are tectosilicates and have a structure which is built up from $TO_4$ tetrahedra that are connected via the oxygens. In the case of the ZAGs, the T atoms represent either quadrivalent silicon or trivalent gallium. These $TO_4$ tetrahedra form chains and layers and these, in turn, build up defined cavity systems including ducts and pores with opening widths of molecular dimensions. The opening widths of the ducts and pores determine the accessibility to the internal cavity structure or materials in accordance with their shape and size. As a result, the porous structures have molecular sieve properties. Due to the incorporation of trivalent gallium, the crystalline lattice of the zeolite-like gallosilicates (ZAGs) has an excess negative charge, which is compensated for during synthesis by the presence of cations (usually alkali or alkaline earth ions).

If the alkali or alkaline earth ions are exchanged after the synthesis for protons, effective acidic catalysts which are useful for heterogeneous catalysis are obtained. Because of their molecular sieve properties, the gallosilicate catalysts of this invention have shape-selective properties.

However, the selectivity and, particularly, the activity of the ZAGs are determined not only by their crystalline features or their pore structure, but also by the size of the crystals and the accessibility of the active centers. "Active centers" are strong Broenstedt-sites (bridged hydroxyl groups) which are connected to gallium tetrahedral atoms inside the lattice or weak Lewis-sites connected either to "extra-framework" gallium species or to silanol groups. To achieve the best possible action of the active centers that are present in the crystal, these centers should be distributed as uniformly as possible throughout the crystal.

The presently known ZAGs are synthesized by a hydrothermal process using organic compounds, generally ammonium compounds, which have structure-directing and structure stabilizing functions (as discussed, for example, in European patent application EP 0 327 189 A2). These compounds are often referred to as "templates."

The synthesis methods heretofore used for synthesizing ZAGs have a number of serious disadvantages which preclude their operation on a large industrial scale without contaminating the environment. The templates used (generally tetraalkylammonium compounds) are toxic, easily inflammable and highly corrosive. Since the synthesis is a hydrothermal reaction that is carried out under high pressure, the escape of these template materials cannot be prevented completely. There is therefore a high potential for endangering the employees and the environment both near and far from the production site. The effluent resulting from the synthesis also contains these template materials and must therefore be treated and disposed of at high cost to prevent environmental contamination. A further disadvantage is the need to burn out (i.e., calcine) the organic components in the lattice at high temperatures. As a result, the templates or their decomposition or breakdown products reach the waste air and must be removed by expensive filtering methods. Calcining can also damage the lattice structure of the ZAGs, adversely affecting their catalytic and adsorptive properties. Moreover, calcining can lead to mechanical damage to the ZAGs.

In addition to the cost and environmental danger resulting from the use of templates, the broad distribution of particle sizes resulting from known synthesis methods is also disadvantageous. This broad distribution of particle sizes decreases the stability and useful life of the ZAGs, as measured by their catalytic properties. Moreover, known ZAGs have an unsatisfactorily inhomogeneous distribution of active centers, which unfavorably affects the selectivity and conversion rate for catalytic reactions.

OBJECT OF THE INVENTION

It is, therefore, an object of the present invention to obtain new, crystalline, zeolite-like gallosilicates with improved properties, from which catalysts with a higher stability and improved long-term catalytic behavior can be prepared. At the same time, it is an object of the invention to obtain catalysts with increased activity, but with undiminished selectivity. The new gallosilicates are particularly suitable for preparing catalysts for the transformation of short-chain hydrocarbons. A further object of the present invention is to obtain a non-polluting method for synthesizing such crystalline, zeolite-like gallosilicates which avoids the use of templates.

SUMMARY OF THE INVENTION

The invention relates to a crystalline zeolite-like gallosilicate having an atomic ratio of Si/Ga in the outer crystalline surface that is not larger than the average Si/Ga ratio for the whole of the crystal.

The invention also relates to a method of making such a gallosilicate comprising the hydrothermal crystallization of a strictly inorganic reaction mixture having the following molar ratios:

$SiO_2/Ga_2O_3 \geq 5$ $OH^-/SiO_2 = 0.05-1.0$ $H_2O/SiO_2 = 10-1,000.$

The invention further relates to the above-described method wherein said reaction mixture is prepared by adding an aged gel to a first mixture, the first mixture preferably having a composition with the following molar ratios:

$SiO_2/Ga_2O_3 \geq 5$ $OH^-/SiO_2 = 0.05$ to $1.0$ $H_2O/SiO_2 = 20$ to $100.$

DETAILED DESCRIPTION OF THE INVENTION

Figure 1:
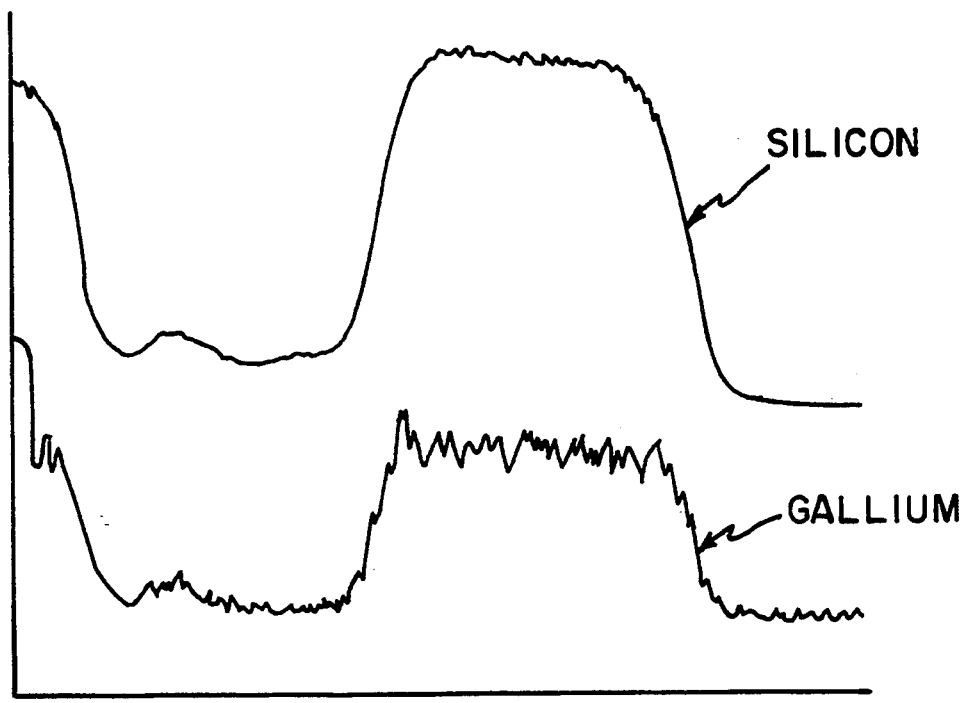
FIG. 1 is a graphical representation of the silicon and gallium distribution over a cross section of a crystal of gallosilicate prepared as described in Example 1.

The gallosilicate of the present invention has a homogeneous distribution of the Si and Ga atoms throughout the crystal. The value of the molar ratio of Si to Ga at the outer surface of the crystal is substantially the same as the average value of this ratio for the entire crystal. Due to the homogeneous distribution of the Ga atoms, the active centers are distributed uniformly throughout the entire crystal. This results in higher total activity for the catalysts prepared from the gallosilicate of the invention. The gallium distribution is believed to result in higher long-term stability for the catalysts, since the degalliation, that is the dissolution of Ga atoms due to thermal stresses (=deactivation) under catalysis conditions, is greatly reduced. This stabilization is believed to be further intensified by the narrower particle size distribution of the gallosilicate of the invention. Furthermore, the catalysts, prepared from the new gallosilicate can withstand higher thermal and hydrothermal stresses.

In a preferred embodiment, the gallosilicate of the invention contain one or more ions from the group comprising $H^+$, $Na^+$ and $NH_4^+$ or cations of a metal from sub-group VIII of the periodic table. These ions can be ion exchanged into the ZAGs using methods that are customarily employed for this purpose.

The optimum composition range for each of the constituents of the new gallosilicate (in dehydrated form) is described by the following ratios:

$0.9 \pm 0.2$ $M_{2/n}$: $Ga_2O_3$: 5–1,000 $SiO_2$ wherein M is a cation and n its valence. Moreover, the gallosilicates of the invention should have at least the interlattice plane distances given in Table 1.

TABLE 1

| Interlattice Plane Distances d of the Gallosilicates Synthesized in Examples 1 to 3 | |
|---|---|
| d (Angstroms) | Diffraction Intensity |
| 11.2 ± 0.2 | strong |
| 10.0 ± 0.2 | strong |
| 6.4 ± 0.1 | weak |
| 5.95 ± 0.1 | weak |
| 5.6 ± 0.1 | weak |
| 3.87 ± 0.05 | strong |
| 3.83 ± 0.05 | strong |
| 3.76 ± 0.05 | weak |
| 3.74 ± 0.05 | moderately strong |
| 3 66 ± 0.05 | weak |
| 2.01 ± 0.02 | weak |
| 1.99 ± 0.02 | weak |

The gallosilicate of the invention can be synthesized easily from strictly inorganic reaction formulations by hydrothermal crystallization in an autoclave. The reaction mixture used in practising the method of the invention consists of water and caustic soda solution, as well as of $SiO_2$ (amorphous) and $Ga_2O_3$ or their hydrated derivatives or alkali silicates, alkali gallates or their salts. The molar ratios of the constituents in the reaction mixture are adjusted to the following values:

$SiO_2/Ga_2O_3 \geq 5$ $OH^-/SiO_2 = 0.05–1.0$ $H_2O/SiO_2 = 10–1,000$.

The method of the present invention does not require templates and, accordingly, is nonpolluting. Moreover, the method avoids the formation of a broad particle size distribution in the product. Additionally, since calcining to burn out organic materials is not necessary, the risk of damaging the product in this way is eliminated completely.

The reaction preferably takes place at temperatures between 40° and 300° C. and under autogenous pressure. Below 40° C., the conversion reaction proceeds slowly and uneconomically, while above 300° C. there is a danger that the gallosilicate product will be unsatisfactory due to the formation of quartz and/or cristobalite. In a particularly preferred embodiment, the reaction takes place at temperatures between 150° and 225° C.

As already mentioned, calcining is not required in practising the method of the present invention. The gallosilicate produced can, therefore, be subjected to an ion exchange directly after the crystallization reaction.

To accelerate the crystallization reaction, it has proven advantageous to add to the reaction mixture an aged, but still x-ray amorphous gallosilicate nucleating gel with an atomic ratio of Si to Ga of $\geq 5$. In this way, the gallosilicate product formed is stabilized and the formation of undesirable secondary phases, such as quartz and cristobalite, is suppressed. Preferably, a nucleating gel with the following molar ratios is used:

$SiO_2/Ga_2O_3 \geq 5$ $OH^-/SiO_2 = 0.01$ to $1.0$ $H_2O/SiO_2 = 10$ to $1,000$.

Preferably, the $H_2O/SiO_2$ ratio and the $OH^-/SiO_2$ ratio of the nucleation gel are less than or equal to the corresponding ratios for the final reaction mixture. More preferably, these ratios are less than the ratios for the final reaction mixture. The nucleating gel preferably is added to a reaction mixture with the following molar composition:

$SiO_2/Ga_2O_3 \geq 5$ $OH^-/SiO_2 = 0.05$ to $1.0$ $H_2O/SiO_2 = 20$ to $100$.

Basically, the aged nucleating gel can be added in any amount to the reaction mixture. Advantageously, however, the amount added should not exceed a value of 50% by weight of the total formulation; preferably, the amount is no more than 25% of the total.

The purpose of aging is to form x-ray amorphous nuclei which accelerate and stabilize the high temperature formation of ZAGs in the final gel. A preferred process for preparing a nucleating gel is described below. A silica source (preferably amorphous pyrogenic silica) is mixed with a solution of NaOH and an acidic solution of a gallium compound (e.g., $GaCl_3$ in Hcl) to achieve a solution with the above-decribed composition ratios. The solution is then stirred under atmospheric pressure at a temperature between 0° and 100° C. for a period of between about 2 hours and 100 days.

Because they possess the properties mentioned above, the gallosilicates of the present invention have proven to be particularly suitable for the preparation of catalysts and adsorbents. The advantageous catalytic properties are demonstrated particularly by use of such catalyts in the aromatization of low molecular weight hydrocarbons. These reactions take place at temperatures between 300° and 800° C., at pressures between 0.1 and 100 bar and at catalyst loads of 0.1 to 100 $h^{-1}$ WHSV (=weight hour space velocity). Preferred ranges for such application are temperatures of 400° to 600° C., pressures of 1 to 10 bar and catalyst loads of 1 to 10 $h^{-1}$WHSV.

The invention is described in greater detail in the following examples which describe various embodiments. Examples 1 to 3 relate to gallosilicates of the present invention, which were synthesized without a template. For comparison purposes, a gallosilicate was synthesized using a template in Example 4.

The distribution of the elements, silicon and gallium, over the cross section of the gallosilicates crystals was determined by using an electron beam microprobe IEOL IXA-773 connected to a PDP 11/23 DEC computer. The samples were embedded in resin (e.g., Araldit Epoxial, available from the Loco Co., Germany), ground with diamond paste (such as that available from Technischer Bedarf Hindelday (TBH) having a granulation of 1 $\mu$m) and sputtered with gold. The electron beam measurements were carried out with an output voltage of 15 kV and a current of 50 $\mu$A. For the samples from Examples 1 to 3 below, the deflection of the electron beam was measured, with the indicated distribution of the elements and the scanning electron microscope photographs recorded on photographic paper (line profile). For the sample from Example 4, the measurement was carried out by moving the sample stepwise under the electron beam with a step width of 1 $\mu$m (line scan). The values obtained were evaluated by computers and the distribution of the elements was recorded by a plotter.

Figure 2:
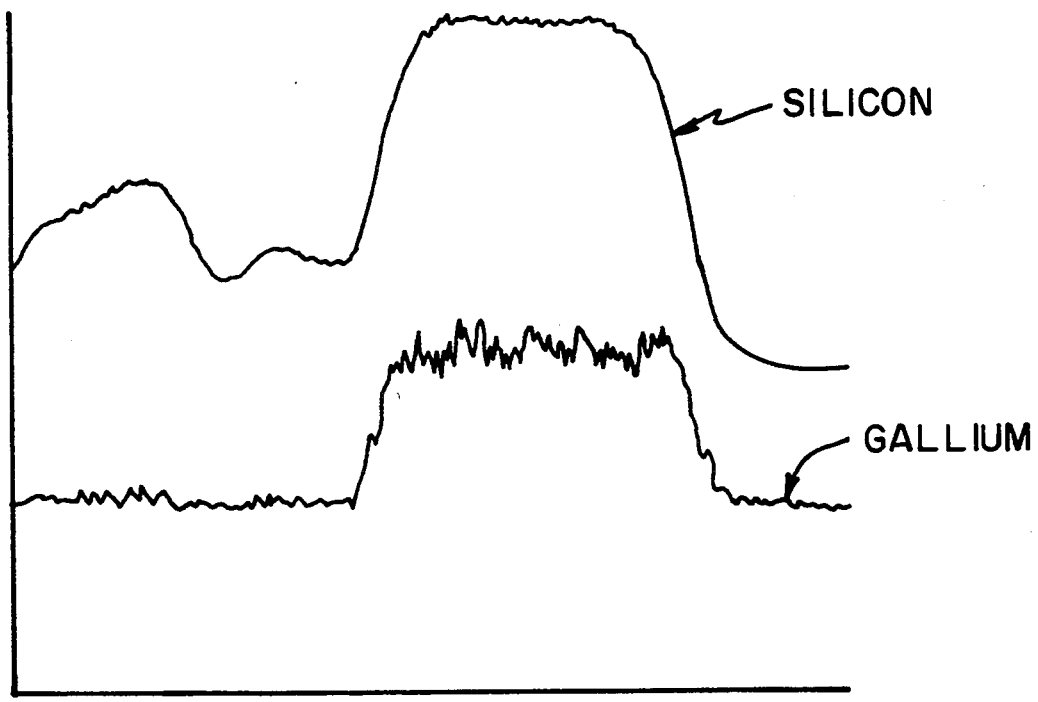
FIG. 2 is a graphical representation of the silicon and gallium distribution over a cross section of a crystal of gallosilicate prepared as described in Example 2.
Figure 3:
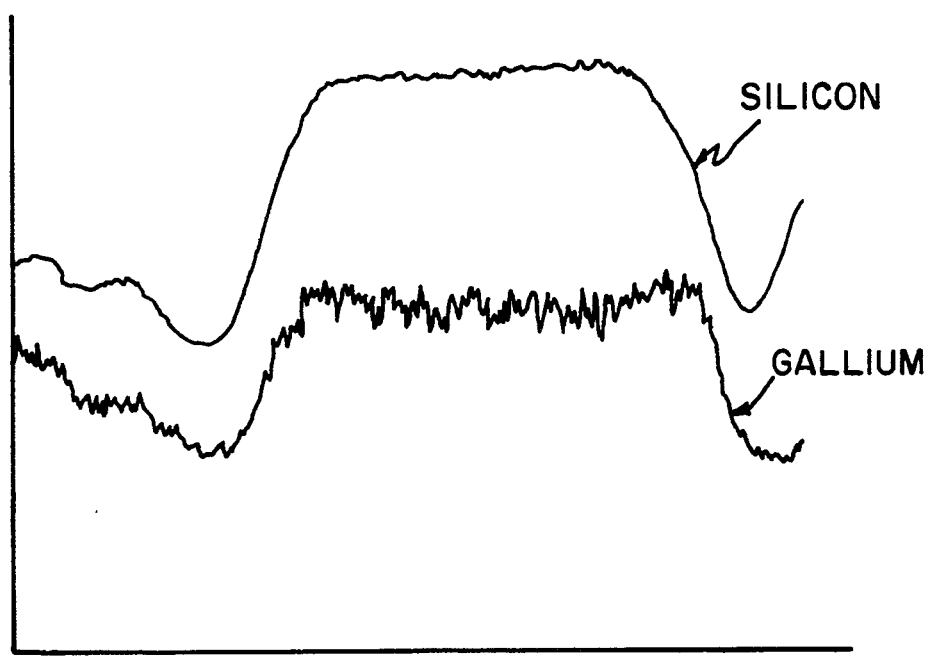
FIG. 3 is a graphical representation of the silicon and gallium distribution over a cross section of a crystal of gallosilicate prepared as described in Example 3.
Figure 4:
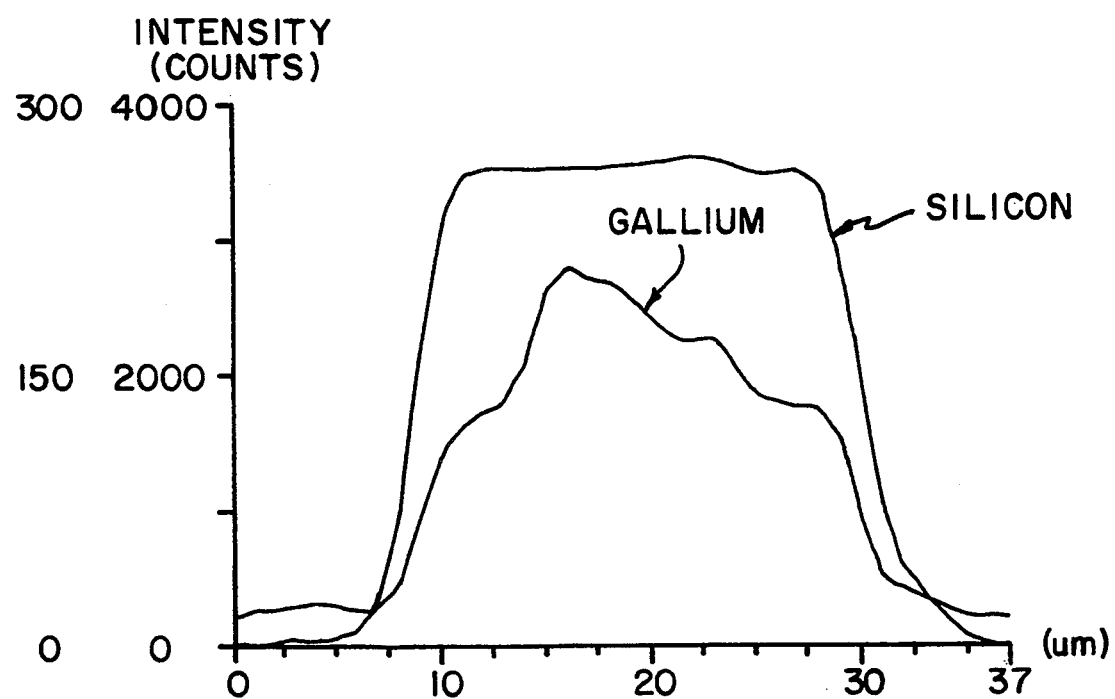
FIG. 4 is a graphical representation of the silicon and gallium distribution over a cross section of a crystal of gallosilicate prepared as described in Example 4.

As shown by the electron beam microanalysis, the inventive ZAGs (Examples 1 to 3) have a uniform Si to Ga atomic ratio over the whole of the crystal (FIGS. 1 to 3). Moreover, the value of the atomic ratio of Si to Ga at the outer crystalline surface is not larger than the average value of this ratio in the whole of the crystal. On the other hand, the sample synthesized with a template (Example 4) shows a ratio of Si to Ga atoms which decreases clearly towards the center of the crystal (FIG. 4).

It will be recognized that the Ga/Si ratio may be difficult to measure at the extreme boundaries of the crystals. However, over the substantial measurement range where the data is sufficiently stable, the ratio of Ga to Si for the ZAGs according to the invention varies no more than about 20%, preferrably 10%. Particularly, the ratio of Si to Ga in the outer shell is not larger than the average Si to Ga ratio for the whole of the crystal.

In Examples 5 to 8, the catalytic properties of catalysts from the gallosilicates of Examples 1 to 4 were investigated by means of the conversion of propane to BTX (BTX=Bezene, Toluene, Xylenes) aromatic products. The aromatization of short-chain hydrocarbons is usually carried out with the $C_1$ to $C_4$ fractions, which are obtained by refining crude oil or from steam cracking (W. Hoelderich, Angew. Chemie, Vol. 100, 232; 1988). This conversion of valuable raw materials has clearly been improved by the upgrading method described here. To illustrate this improvement, propane, for example, is converted with high selectivity in a dehydrocyclization reaction, using the catalysts of Examples 1-3, primarily into benzene and toluene. These aromatic materials can be used to improve the pre-ignition resistance of fuels for internal combustion engines (H. G. Franck, B. W. Stadelhofer, "Industrielle Aromatenchemie (Chemistry of Industrial Aromatic Materials)", Springer Verlag, Berlin 1987), or as starting materials for the organic chemistry industry.

The catalytic investigations of Examples 5 to 8 were carried out in a microreactor, wherein the reactions occurred in a flow pipe. The catalyst, which is diluted with quartz fill, fills a segment of the flow pipe through which the reaction gas ($C_2$ to $C_4$ aliphatic material, preferably propane) flows. The flow of gas is controlled by needle valves. The reactor is heated by a tube furnace, which is controlled by a thermocouple which extends into the catalyst fill. Prior to the reaction, the catalysts are calcined in the reactor, generally at a temperature of about the reaction temperature. After flushing the reactor for about thirty minutes with nitrogen at a temperature which is generally close to the reaction temperature, the reaction gas is passed through the reactor. The reaction product mixture is analyzed using an on-line gas chromatograph.

Example 1: Preparation of Gallosilicates

Amorphous, pyrogenic silica (41.68 g) was homogenized with 12.44 g of NaOH and 2.59 g of $GaCl_3$ solution (contains 0.77 g of gallium) in 1,000 g of water while stirring for 30 minutes. This reaction formulation, with the molar ratios of $H_2O/SiO_2=80$, $SiO_2/Ga_2O_3=129$ and $OH^-/SiO_2=0.42$, was placed in a teflon-lined autoclave with a nominal capacity of 1.5 L and reacted for 5 days at 433K under autogenous pressure.

After filtering and washing with water, about 30 g of a crystalline gallosilicate with a molar ratio of $SiO_2$ to $Ga_2O_3$ of 95 was obtained, which showed the x-ray diffractions corresponding to at least the interlattice plane distances listed in Table 1 and had a homogeneous distribution of gallium throughout the crystals (as shown in FIG. 1).

Example 2: Preparation of Gallosilicates

Amorphous, pyrogenic silica (50.012 g) was homogenized with 13.317 g of NaOH and 12.77 g of $GaCl_3$ solution (contains 1.935 g of gallium) in 600 g of water by stirring for 30 minutes. This mixture, which had molar ratios of $H_2O/SiO_2=40$, $SiO_2/Ga_2O_3=60$ and $OH^-/SiO_2=0.3$, was aged for 30 days at 298K under atmospheric pressure with stirring.

Subsequently, a second, well homogenized mixture of 20.839 g of amorphous, pyrogenic silica, 9.092 g of NaOH and 5.343 g of GaCl₃ solution (contains 0.809 g of gallium) in 1,100 g of water was added and the reaction formulation, with the resulting molar ratios of $H_2O/SiO_2=80$, $SiO_2/Ga_2O_3=60$ and $OH^-/SiO_2=0.375$ was transferred to a stainless steel autoclave with a capacity of 2 L and reacted for 32 hours at 453K under autogenous pressure and with stirring.

After filtering and washing with water, about 40 g of a crystalline gallosilicate with a molar ratio of $SiO_2$ to $Ga_2O_3$ of 42 was obtained, which showed at least the x-ray diffractions corresponding to the interlattice plane distances listed in Table 1 and has a homogeneous distribution of the gallium throughout the crystals (as shown in FIG. 2).

Example 3: Preparation of Gallosilicates

Amorphous, pyrogenic silica (29.173 g) was homogenized with 8.73 g of NaOH and 11.178 g of GaCl₃ solution (contains 1.593 g of gallium) in 350 g of water by stirring for 30 minutes. This mixture, with the molar ratios of $H_2O/SiO_2=40$, $SiO_2/Ga_2O_3=40$ and $OH^-/SiO_2=0.3$ was aged for 7 days at 363K under atmospheric pressure. Subsequently, an inert, well-homogenized mixture of 12.501 g of amorphous, pyrogenic silica, 5.826 g of NaOH and 4.781 g of GaCl₃ solution (contains 0.724 g of gallium) in 350 mL of water is added and the resultant reaction formulation, with the molar ratios of $H_2O/SiO_2=80$, $SiO_2/Ga_2O_3=40$ and $OH^-/SiO_2=0.375$, was reacted in a stainless steel autoclave with a nominal capacity of 1 L for 21 hours at 453K with stirring under autogenous pressure.

After filtering and washing with water, about 25 g of a crystalline gallosilicate with a molar ratio of $SiO_2$ to $Ga_2O_3$ of 26 was obtained, which showed at least the x-ray diffraction corresponding to the interlattice plane distances listed in Table 1 and had a homogeneous distribution of gallium throughout the crystals (as shown in FIG. 3).

Example 4 (Comparison Example): Prior Art Preparation of Gallosilicates

Colloidal silica sol (6.615 g containing 2.778 g of $SiO_2$) was homogenized with 1.723 g of tetrapropylammonium bromide ("TPABr"), 0.445 g of GaCl₃ solution (contains 0.067 g of gallium) and 3.238 g of hexamethylenetetramine ("HMT") in 25 g of water while stirring for 90 minutes.

This reaction formulation, with the molar ratios of $H_2O$ $SiO_2=30$, $SiO_2/Ga_2O_3=92$, $HMT/SiO_2=0.5$, $TPABr/SiO_2=0.14$, was placed in a teflon-lined autoclave with a nominal capacity of 50 mL and reacted at 453K for four days under autogenous pressure. After filtration and washing with water, approximately 2 g of a crystalline, alkali-free gallosilicate with a molar ratio of $SiO_2$ to $Ga_2O_3$ of 92 is obtained, which had showed x-ray diffractions corresponding to at least the interlattice plane distances listed in Table 1 and had a nonuniform distribution of the gallium (heavy accumulation of gallium in the interior of the crystals) over a cross-section of the crystals (as shown in FIG. 4).

Example 5: Preparation and Use of a Catalyst Prepared from the Gallosilicate of Example 1

The gallosilicate prepared in Example 1 was converted to the ammonium form by ion exchanging it three times with a 1 molar ammonium nitrate solution at 95° C. for two hours. At the end of each ion exchange process, the product was washed with distilled water. After being dried at 120° C. for 12 hours, the gallosilicate was formed into extrudates with 30% by weight of an amorphous silica by the method described in the EP 0 403 966 A1 and activated for 12 hours at 550° C. in a stream of nitrogen. At a reaction temperature of 530° C. and a WHSV of 1 h⁻¹ (gr. propane/gr. catalyst/hour), the catalyst showed a propane conversion of 15.3% with a selectivity for BTX aromatic compounds of 42% (see Table 2, below).

Example 6: Preparation and Use of a Catalyst Prepared from the Gallosilicate of Example 2

The gallosilicate prepared in Example 2 was converted to the ammonium form by being ion exchanged three times with a 1 molar ammonium nitrate solution at 95° C. for 2 hours. At the end of each ion exchange process, the product was washed with distilled water. After being dried at 120° C. for 12 hours, the gallosilicate was formed into extrudates with 30% by weight of an amorphous silica by the method described in EP 0 403 966 A1 and activated for 12 hours at 550° C. in a stream of nitrogen.

At a reaction temperature of 530° C. and a WHSV of 1 h⁻¹ (gram of propane/gram of catalyst/hour), the catalyst showed a propane conversion of 24.1% with a selectivity for BTX aromatic compounds of 50% (see Table 2, below).

Example 7: Preparation and Use of a Catalyst Prepared from the Gallosilicate of Example 3

The gallosilicate prepared in Example 3 was converted to the ammonium form by being ion exchanged three times with a 1 molar ammonium nitrate solution at 95° C. for 2 hours. At the end of each ion exchange process, the product was washed with distilled water. After being dried at 120° C. for 12 hours, the gallosilicate was formed into extrudates with 30% by weight of an amorphous silica by the method described in EP 0 403 966 A1 and activated for 12 hours at 550° C. in a stream of nitrogen.

At the reaction temperature of 530° C. and a WHSV of 1 h⁻¹ (gram of propane/gram of catalyst/hour), the catalyst showed a propane conversion of 40.5% with a selectivity for BTX aromatic compounds of 51% (see Table 2, below).

Example 8 (Comparative): Preparation and Use of a Catalyst Prepared from the Gallosilicate of Example 4

The gallosilicate prepared in Example 4 was converted by calcining for 12 hours at 550° C. into the catalytically active H form and subsequently formed into extrudates with 30% by weight of amorphous silica by the method described in EP 0 403 966 A1 and activated for 12 hours at 550° C. in the reactor in a stream of nitrogen. At the reaction temperature of 530° C. and a WHSV of 1 h⁻¹ (gram of propane/gram of catalyst/hour), the catalyst showed a propane conversion of 2.8% with a selectivity for BTX aromatic compounds of 40% (see Table 2, below).

TABLE 2

| Propane Aromatizing Properties of Inventive Catalysts (Examples 5 to 7) and a Comparison Catalyst (Example 8) | | | |
|---|---|---|---|
| Example No. | $SiO_2/Ga_2O_3$ (moles/mole) | Conversion (%) | Selectivity to BTX Aromatic Compounds (%) |
| 5 | 95 | 15.3 | 42 |
| 6 | 42 | 24.1 | 50 |

TABLE 2-continued

Propane Aromatizing Properties of
Inventive Catalysts (Examples 5 to 7)
and a Comparison Catalyst (Example 8)

| Example No. | $SiO_2/Ga_2O_3$ (moles/mole) | Conversion (%) | Selectivity to BTX Aromatic Compounds (%) |
|---|---|---|---|
| 7 | 26 | 40.5 | 51 |
| 8 | 92 | 2.8 | 40 |

The results of these and other investigations to compare inventive ZAGs, which have a uniform distribution of gallium, with ZAGs with a nonuniform distribution of metal, can be summarized as follows:

1) Aliphatic as well as cycloaliphatic materials (branched and unbranched, saturated or unsaturated) with a number of carbon atoms from two to six can be aromatized on all the ZAGs investigated (wherein the conditions used in the experiments were: 400° C.<T<600° C.; 0.1 bar<p<100 bar; 0.1 $H^{-1}$<WHSV<100 $h^{-1}$);

2) Under the same reaction conditions (temperature, WHSV, pressure), ZAGs with higher proportions of gallium have higher conversions and similar selectivities with respect to the formation of BTX aromatic compounds than those with lower proportions of gallium;

3) Catalysts from the gallosilicates of the present invention with a homogeneous distribution of Ga over any cross section of the crystals have clearly higher conversions with at least constant selectivity with respect to the formation of BTX aromatic compounds than catalysts from gallosilicates with an accumulation of Ga in the interior of the crystals.

We claim:

1. A crystalline structure comprising a gallosilicate composition, said structure belonging to the crystallographic family of tectosilicates and built up from $TO_4$ tetrahedra that are connected by oxygen atoms, wherein T represents a quadrivalent silicon or a trivalent gallium, said structure having an outer surface, said outer surface having an Si to Ga atomic ratio that is less than or equal to the average Si to Ga atomic ratio for the whole crystal;

said composition having an homogenous distribution of Si and Ga atoms throughout the crystal;

wherein said composition is formed without a template.

2. The crystalline structure of claim 1, wherein said structure contains one or more ions selected from the group consisting of $H^+$, $Na^+$, $NH_4^+$ or cations of a metal of sub-group VIII of the Periodic Table.

3. The crystalline structure of claim 1, wherein, in the dehydrated form, said structure has the following chemical composition ratios:

0.9±0.2 $M_{2/n}$ : $Ga_2O_3$ : 5–1,000 $SiO_2$ wherein M is a cation and n its valence.

4. The crystalline structure of claim 3, wherein said structure displays X-ray diffractions corresponding to at least the interlattice plane distances (d) listed below:

d (Angstroms)
11.2±0.2
10.0±0.2
6.4±0.1
5.95±0.1
5.6±0.1
3.87±0.05
3.83±0.05
3.76±0.05
3.74±0.05
3.66±0.05
2.01±0.02
1.99±0.02.

5. The crystalline structure of claim 4, wherein said diffractions are of the relative intensity listed below:

| d (Angstroms) | Intensity |
|---|---|
| 11.2 ± 0.2 | strong |
| 10.0 ± 0.2 | strong |
| 6.4 ± 0.1 | weak |
| 5.95 ± 0.1 | weak |
| 5.6 ± 0.1 | weak |
| 3.87 ± 0.05 | strong |
| 3.83 ± 0.05 | strong |
| 3.76 ± 0.05 | weak |
| 3.74 ± 0.05 | moderately strong |
| 3.66 ± 0.05 | weak |
| 2.01 ± 0.02 | weak |
| 1.99 ± 0.02 | weak. |

6. A method of converting $C_2$ to $C_4$ aliphatic hydrocarbons to BTX aromatic compounds comprising passing a gas comprising $C_2$ to $C_4$ aliphatic hydrocarbons through a reactor comprising crystalline gallosilicate structures belonging to the crystallographic family of tectosilicates and built up from $TO_4$ tetrahedra that are connected via oxygen atoms, wherein T represents a quadrivalent silicon or a trivalent gallium, said structures having outer surfaces, said outer surfaces having an Si to Ga atomic ratio that is less than or equal to the average Si to Ga atomic ratio for each whole crystal;

said composition having an homogenous distribution of Si and Ga atoms throughout the crystal;

wherein said composition is formed without a template, and recovering BTX aromatic compounds from the effluent of said reactor.

7. The method of converting $C_2$ to $C_4$ aliphatic hydrocarbons to BTX aromatic compounds according to claim 6, wherein said method includes pressure which ranges between about 0.1 and about 100 bar, said temperature between about 300° and about 800° C. and a velocity between about 0.1 and about 100 $h^{-1}$ WHSV.

8. The method of converting $C_2$ to $C_4$ aliphatic hydrocarbons to BTX aromatic compounds according to claim 6, wherein said method includes temperature which range between about 400° and about 600° C., a pressure which ranges between about 1 and about 10 bar and a velocity which ranges between about 1 and about 10 $h^{-1}$ WHSV.

9. A crystalline structure comprising a gallosilicate composition consisting of tectosilicates and built up from $TO_4$ tetrahedra that are connected by oxygen atoms, wherein T represents a quadrivalent silicon or a trivalent gallium, said structure having an outer shell of said crystalline structure having an Si to Ga atomic ratio that is less than or equal to the average Si to Ga atomic ratio for the whole crystal;

said composition having an homogenous distribution of Si and Ga atoms throughout the crystal;

wherein said composition is formed without a template.

* * * * *